United States Patent [19]
Winn

[11] 3,931,001
[45] Jan. 6, 1976

[54] PENTACHLOROPHENOL RECOVERY WITH METHYLENE CHLORIDE

[75] Inventor: William D. Winn, Lake Jackson, Tex.

[73] Assignee: The Dow Chemical Company, Midland, Mich.

[22] Filed: June 14, 1974

[21] Appl. No.: 479,340

[52] U.S. Cl. .................. 210/22; 203/10; 203/39; 203/67
[51] Int. Cl.² .................. B01D 3/00; B01D 11/00
[58] Field of Search ........ 260/623 R, 627 R, 627 H; 210/21, 22; 203/10–12, 14, 39, 43–46, 67, DIG. 5

[56] References Cited
UNITED STATES PATENTS

| | | | |
|---|---|---|---|
| 2,761,563 | 9/1956 | Waterman et al. | 260/627 R |
| 3,365,395 | 1/1968 | McDonald | 210/21 |
| 3,692,829 | 9/1972 | Sennewald et al. | 203/43 |

Primary Examiner—Norman Yudkoff
Assistant Examiner—Frank Sever
Attorney, Agent, or Firm—Glwynn R. Baker

[57] ABSTRACT

A method for removing antimicrobials such as pentachlorophenol from waste water by liquid-liquid extraction with a water immiscible organic liquid in a packed column; recovering the antimicrobial from the organic phase by distillation if desired; and, treating of the aqueous phase to remove residual antimicrobial and organic liquid. The process of the present invention recovers about 99 percent of the antimicrobial pentachlorophenol in the waste water producing a waste water containing less than 30 ppm pentachlorophenol and less than about 2 percent organic liquid, both of which may be removed by conventional carbon absorption or soil percolation to acceptable ecological levels for introduction into a stream or reuse as process water.

1 Claim, 1 Drawing Figure

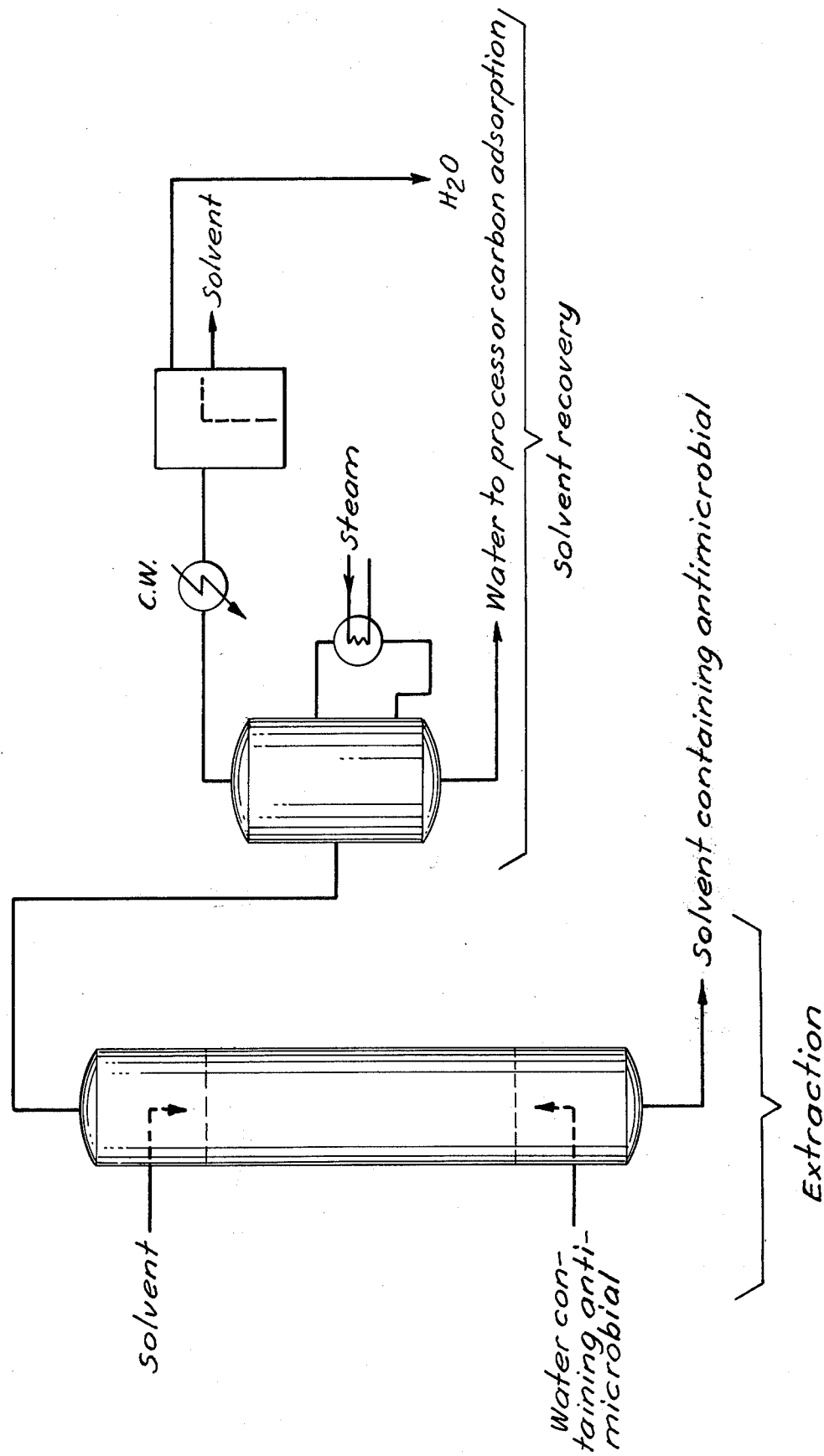

PENTACHLOROPHENOL RECOVERY WITH METHYLENE CHLORIDE

BACKGROUND OF THE INVENTION

The use of pentachlorophenol and other anitmicrobial agents to treat wood and using steam to remove impregnating solvents or using water as the carrier has resulted in aqueous waste water containing the pentachlorophenol and antimicrobials. It is necessary to recover the major portion of the antimicrobial for economic reasons and now necessary to recover the remainder because of ecological reasons. The removal of the pentachlorophenol residue and other antimicrobials in the treating water permits discharge of the water into streams without detrimental effect to the environment. However, more advantageously it permits reuse of the waste in chemical processing, removing any ecological problems and producing an economy in water usage permitting plant site locations off riparian ways.

These and other objects will become apparent to those skilled in the art to which the present invention pertains from the following description.

DESCRIPTION OF DRAWING

The FIGURE shows the preferred embodiment of the invention.

BRIEF DESCRIPTION OF THE INVENTION

In accordance with the present invention a waste water containing an antimicrobial, as for example a waste steaming water from a methylene chloride-pentachlorophenol wood impregnation process, can be treated in a liquid-extraction column by passing the waste water upwardly through a packed column while passing in a counter current manner a water immiscible organic liquid in which pentachlorophenol is soluble. The overhead from the column is water with less than 30 ppm pentachlorophenol and less than about 2 percent organic extractant. The extractant can be removed by distillation or both the organic extractant and pentachlorophenol can be removed by carbon adsorption or soil percolation, water of high purity can be obtained. Likewise since the organic liquid will boil below the pentachlorophenol, the organic extractant can be removed readily by distillation or merely concentrated if it is the organic carrier for the pentachlorophenol or other antimicrobial agent as is the case, for example, in the wood treating process.

Good results have been obtained when the organic extractant is methylene chloride and is used in a ratio of about 1/30 to 1/10 the amount of water to be treated. Further, since methylene chloride boils from 37°C. when slightly wet to 40°C. when dry, it is advantageous to introduce the waste water at a temperature above the boiling point of the extractant and employ pressure to maintain the organic extractant in the liquid phase during extraction. This permits flash evaporation of the organic liquid from the purified water as well as recovery of solvent extractant from the pentachlorophenol or other antimicrobial by simple flash evaporation.

It is of course to be understood that while antimicrobials are described above, and pentachlorophenol in particular, other water insoluble organic materials such as petroleum oils may be removed from water by this technique.

DETAILED DESCRIPTION OF INVENTION

In accordance with the present invention a waste water from a pentachlorophenol-methylene chloride wood treating process containing 0.02 pounds of pentachlorophenol per ten (10) pounds of water was contacted in a counter current packed column at a rate about 0.4 gallons per minute per sq. ft. with one half pound of methylene chloride containing 0.001 pound of water. The waste water was flowed upwardly and the methylene chloride flowed downwardly. The temperature of the incoming streams and liquids in the contacting column were about 20°C. An overhead was taken from the column above the methylene chloride inlet. This overhead contained 0.2 pound methylene chloride, ten (10) pounds water and 15 ppm pentachlorophenol. A bottom stream taken from the tower below the waste water inlet had a composition: 0.3 pound methylene chloride, 0.0006 pound water and 0.02 pound pentachlorophenol. The overhead, water containing 0.2 pound of methylene chloride and 15 ppm pentachlorophenol was heated and the methylene chloride flashed-off. The vapors were condensed, sent to a water separator and 0.15 pounds of methylene chloride were recovered. The water from the flash evaporator was employed as steaming water in a methylene chloride-pentachlorophenol wood impregnating process after suitable treatment to adjust the PH. The water had 15 ppm pentachlorophenol and a trace of methylene chloride. If the water was not to be reused it could be cleaned-up of both pentachlorophenol and the trace of methylene chloride by passing it through a carbon adsorption column, by soil percolation or by biodegradation in ponds. The methylene chloride from the bottom of the column and that from the water separator, a total of 0.4506 pound (90%) and the pentachlorophenol dissolved therein (0.02–0.00015) 99% are available for use in the wood treating process or can be separated by simple distillation.

The present invention may be operated under superatmospheric pressures and temperatures upwards of 200°F, particularly when the waste water is of these higher temperatures as it comes from the primary process. Such temperatures with appropriate pressures enable flash distillations to be accomplished without heating as employed in the example.

What is claimed is:

1. A process for recovering pentachlorophenol from water which comprises:
   a. contacting in a zone the water containing pentachlorophenol in a countercurrent manner with methylene chloride to produce an aqueous phase and a methylene chloride phase;
   b. withdrawing the aqueous phase from the top of said contacting zone;
   c. withdrawing said methylene chloride phase from the bottom of said contacting zone;
   d. heating the withdrawn aqueous phase to distill the methylene chloride from the phase;
   e. discarding the residue of said distillation;
   f. condensing the methylene chloride and water vapors from said distillation;
   g. separating the condensed methylene chloride from said condensed water by decantation;
   h. mixing the methylene chloride so separated with the withdrawn methylene chloride phase from the contacting zone;

said contacting zone being packed to increase the contact of the methylene chloride and the water phases;

said methylene chloride being employed in an amount sufficient to (1) dissolve the pentachlorophenol in the water entering the zone and (2) in an amount in excess of that necessary to saturate the aqueous phase in order to insure phase separation of the water and methylene chloride.

* * * * *

UNITED STATES PATENT AND TRADEMARK OFFICE
CERTIFICATE OF CORRECTION

PATENT NO. : 3,931,001
DATED : January 6, 1976
INVENTOR(S) : William D. Winn

It is certified that error appears in the above—identified patent and that said Letters Patent are hereby corrected as shown below:

Col. 1, line 35, after "liquid-" and before "extraction" insert -- liquid --

Signed and Sealed this thirteenth Day of April 1976

[SEAL]

Attest:

RUTH C. MASON
Attesting Officer

C. MARSHALL DANN
Commissioner of Patents and Trademarks